United States Patent [19]

Knollenberg

[11] Patent Number: 5,282,151
[45] Date of Patent: Jan. 25, 1994

[54] SUBMICRON DIAMETER PARTICLE DETECTION UTILIZING HIGH DENSITY ARRAY

[75] Inventor: Robert G. Knollenberg, Boulder, Colo.

[73] Assignee: Particle Measuring Systems, Inc., Boulder, Colo.

[21] Appl. No.: 662,441

[22] Filed: Feb. 28, 1991

[51] Int. Cl.⁵ .............................................. G01N 15/02
[52] U.S. Cl. ................................. 364/555; 356/335; 356/336
[58] Field of Search ............... 356/335, 336, 337, 338, 356/339, 340, 341, 342, 343; 364/555

[56] References Cited

U.S. PATENT DOCUMENTS

| | | | |
|---|---|---|---|
| 3,669,542 | 6/1972 | Capellaro | 356/336 X |
| 4,075,462 | 2/1978 | Rowe | 235/92 PC |
| 4,636,075 | 1/1987 | Knollenberg | 356/336 |
| 4,710,642 | 12/1987 | McNeil | 250/571 |
| 4,798,465 | 1/1989 | Knollenberg | 356/336 |
| 4,830,494 | 5/1989 | Ishikawa et al. | 356/336 |
| 4,893,928 | 1/1990 | Knollenberg | 356/336 |
| 4,920,275 | 4/1990 | Itoh | 250/574 |

FOREIGN PATENT DOCUMENTS

| | | |
|---|---|---|
| 0300875 | 1/1989 | European Pat. Off. |
| 9010216 | 9/1990 | PCT Int'l Appl. |
| 1497698 | 1/1978 | United Kingdom |

OTHER PUBLICATIONS

Knollenberg "The Measurement of Particle Sizes Below 0.1 Micrometers", Journal of Environmental Sciences, Jan./Feb. 1985, pp. 32–51.

Aikens, "Watch Out Photography, Here Come Cooled HCCD Cameras", Photonics Spectra, Nov. 1990, pp. 95–101.

Primary Examiner—Edward R. Cosimano
Attorney, Agent, or Firm—Robert E. Harris

[57] ABSTRACT

Submicron diameter particle detection utilizing a high density array is disclosed. The high density array, such as a charge coupled device, is utilized to detect light scattered at a sensing region by particles illuminated by a light source, such as a laser source. Charge storage is utilized to buffer each data frame transferred from the high density array and the multiple serial outputs are processed by parallel processing that includes threshold detection and analog-to-digital converting. A microcomputer and associated digital storage receives the digital outputs and provides outputs indicative of submicron particle sizing. Further improvement in minimum detectable particle sizing of particles carried by a fluid is realized by use of beam shaping optics to shape the illumination beam passed through the sensing region to form either an astigmatic (highly elliptical) beam cross-section, with the fluid being directed towards the imaging system orthogonal to the object plane, or a circular beam cross-section with the flow directed parallel to object plane, and with the focal point of the beam being substantially centrally positioned within the sensing region in either case.

35 Claims, 6 Drawing Sheets

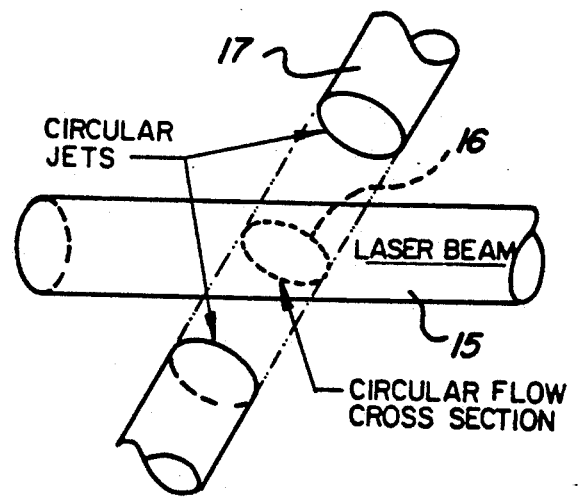
*Fig_1A*
PRIOR ART
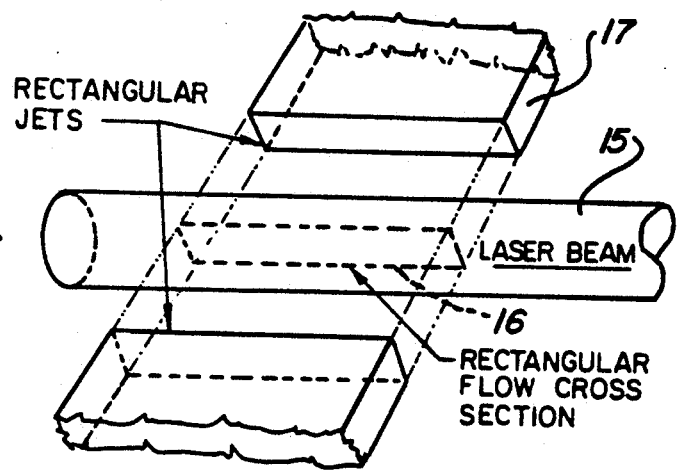
*Fig_1B*
PRIOR ART
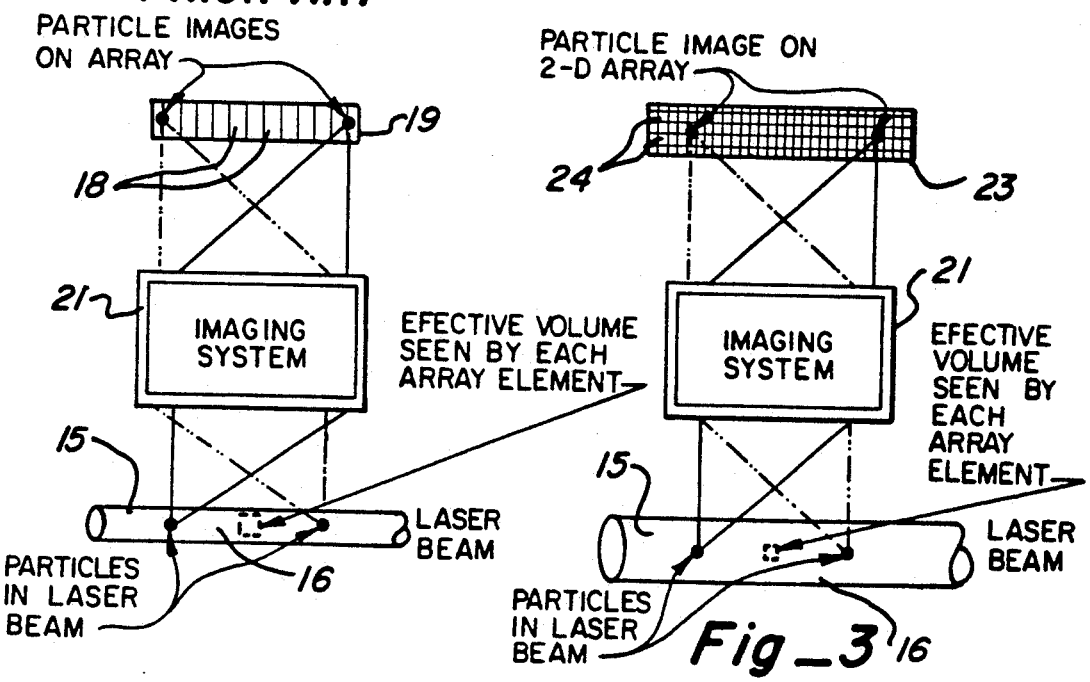
*Fig_2* PRIOR ART
*Fig_3*

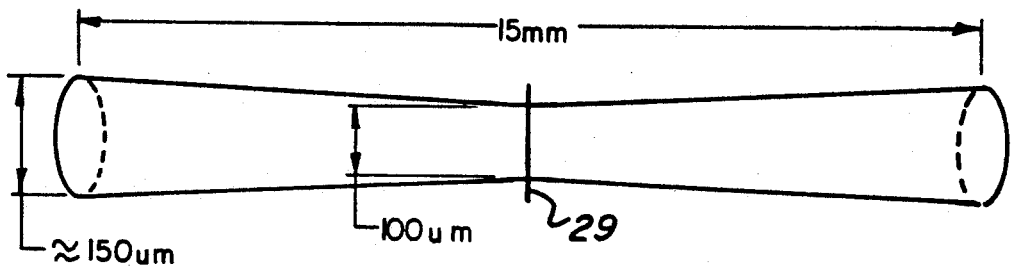
Fig_4B
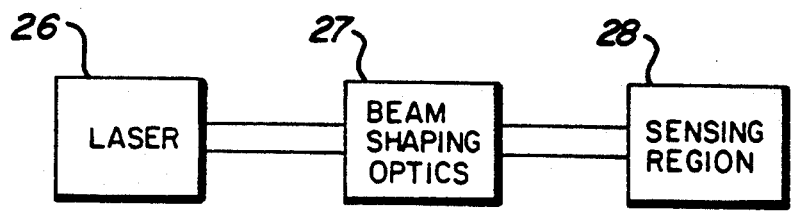
Fig_4A
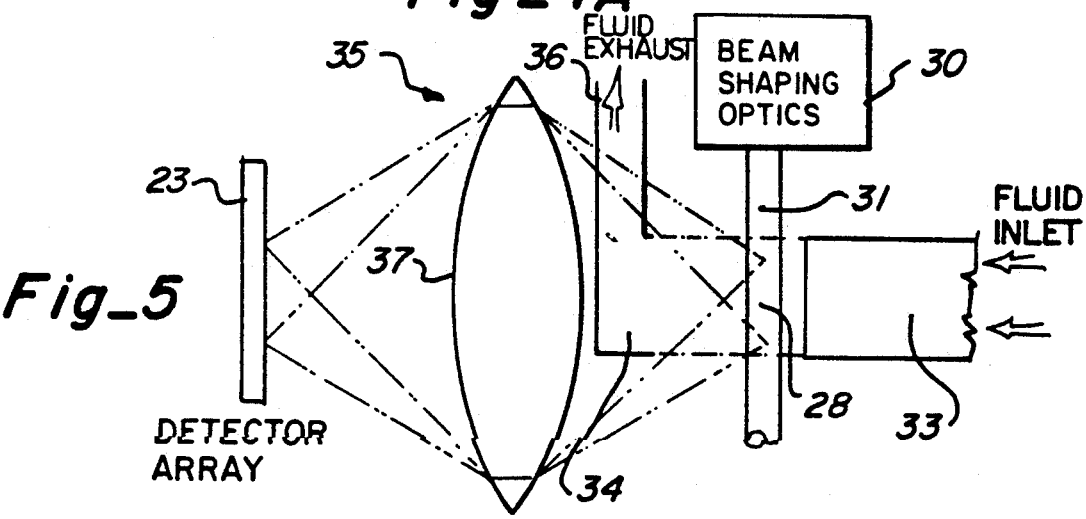
Fig_5
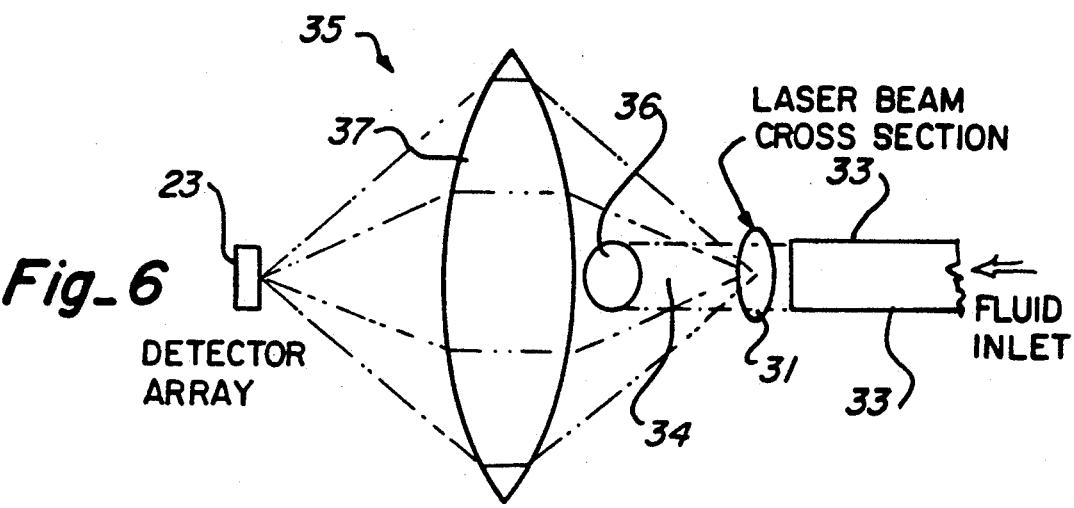
Fig_6

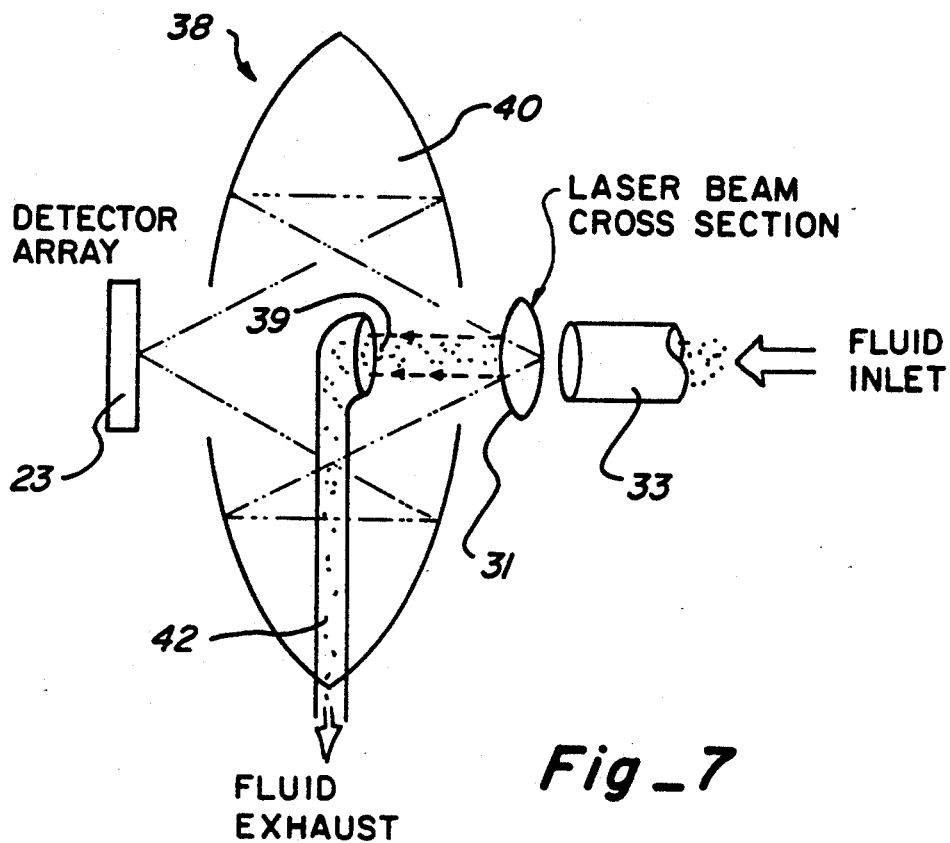
Fig_7
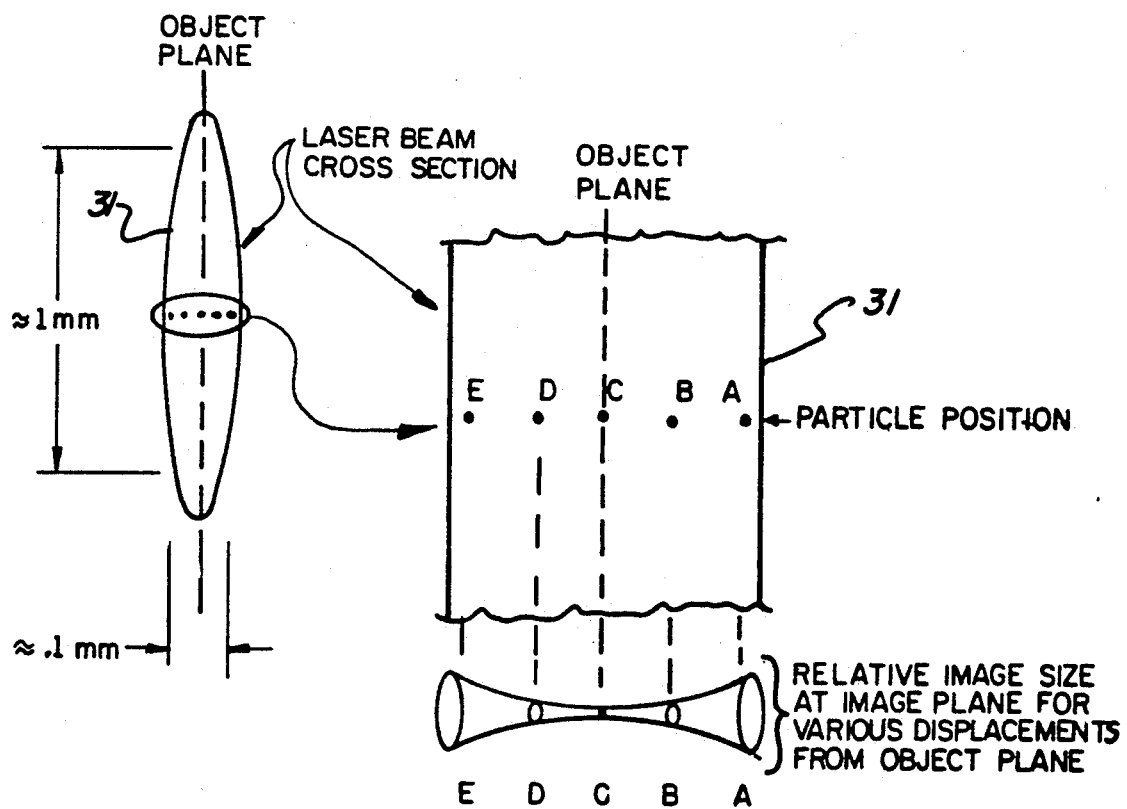
Fig_8

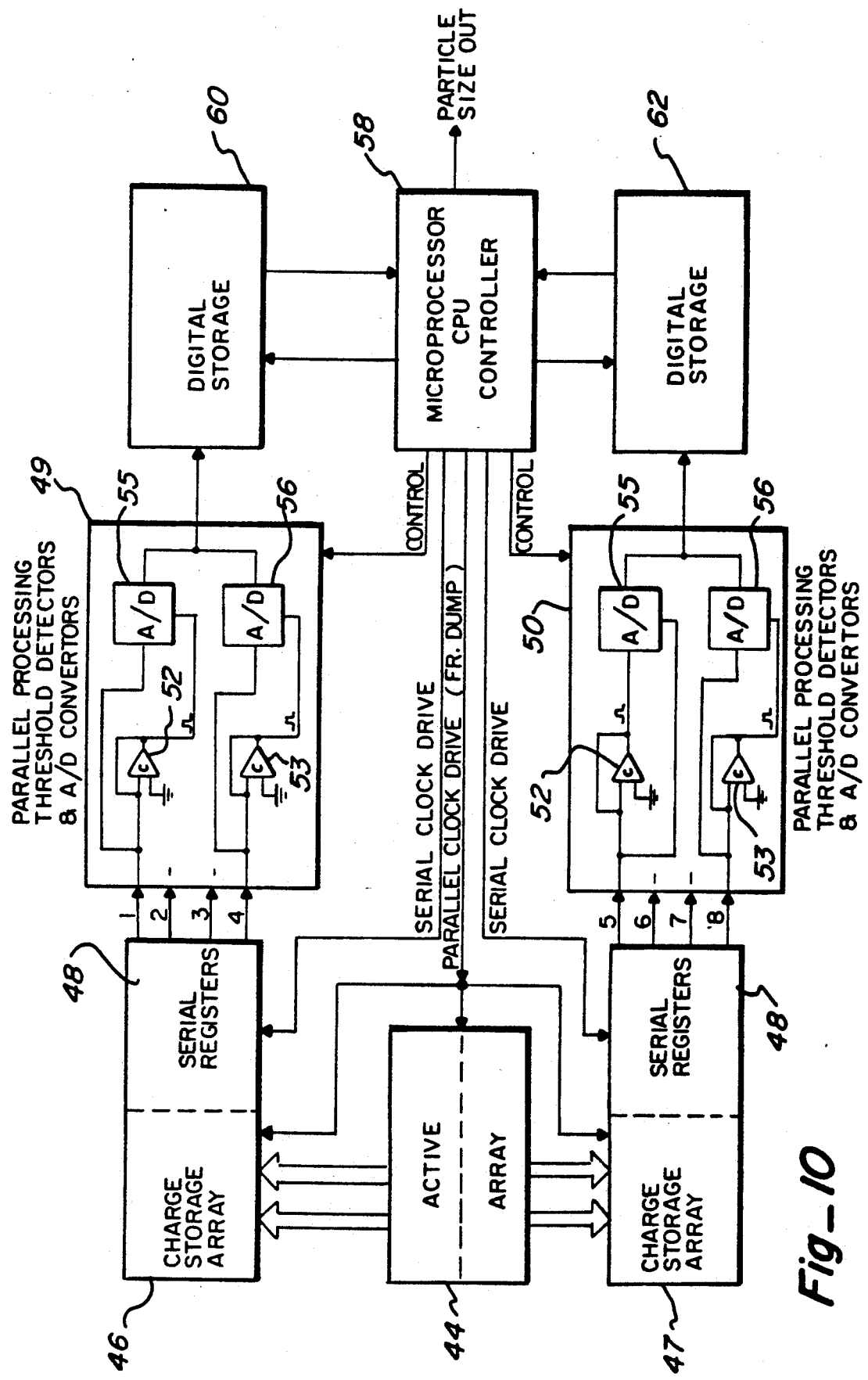
Fig_10

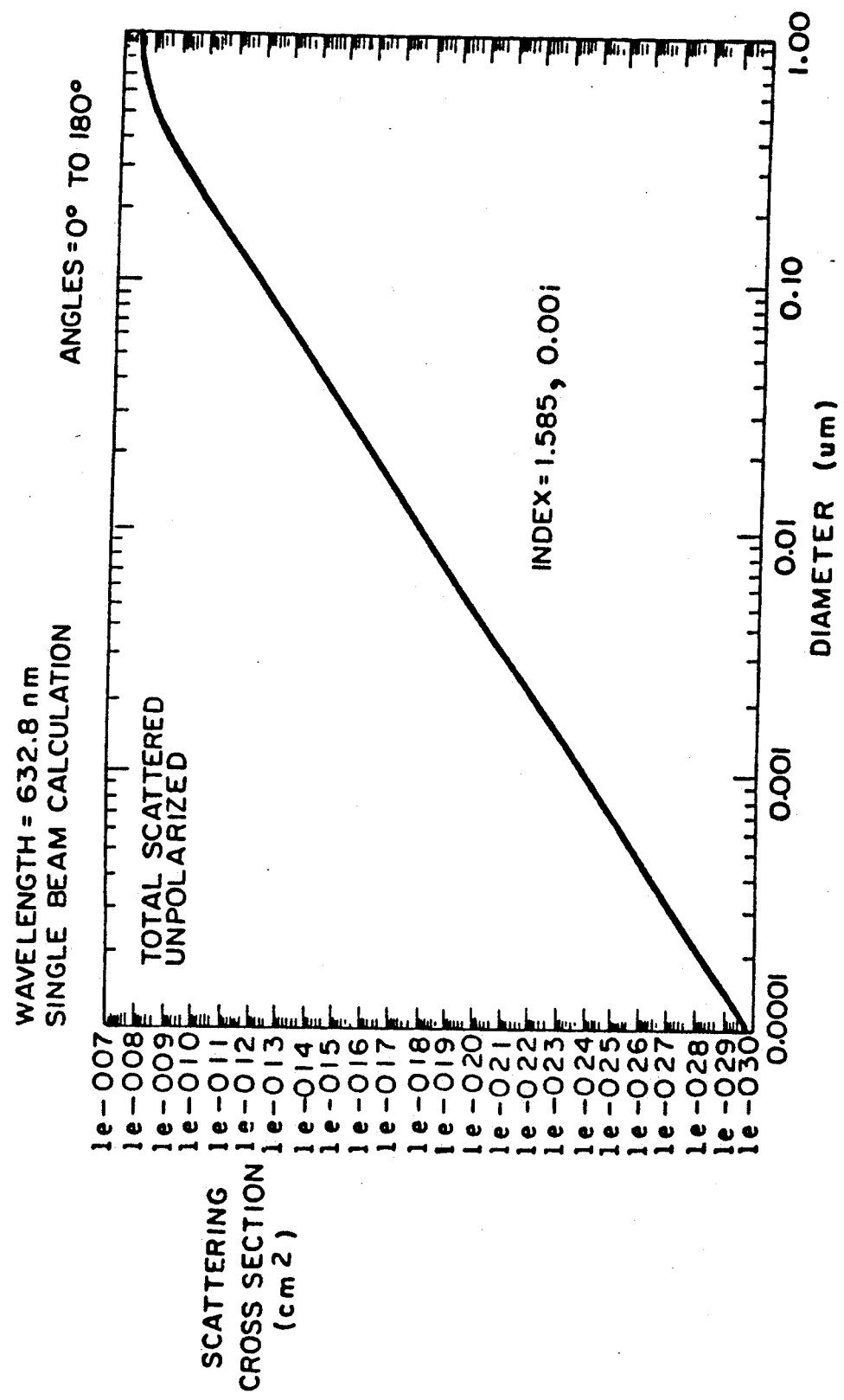
Fig_11

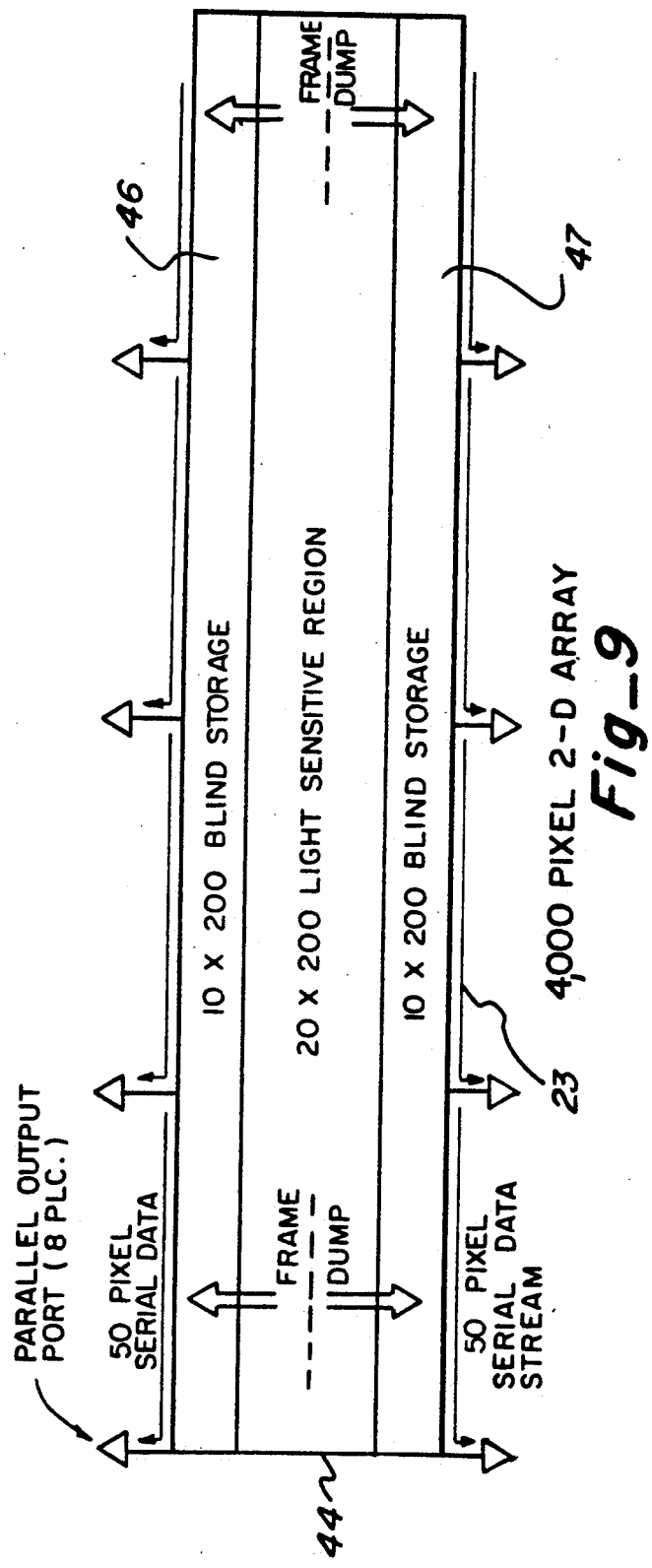
Fig_9
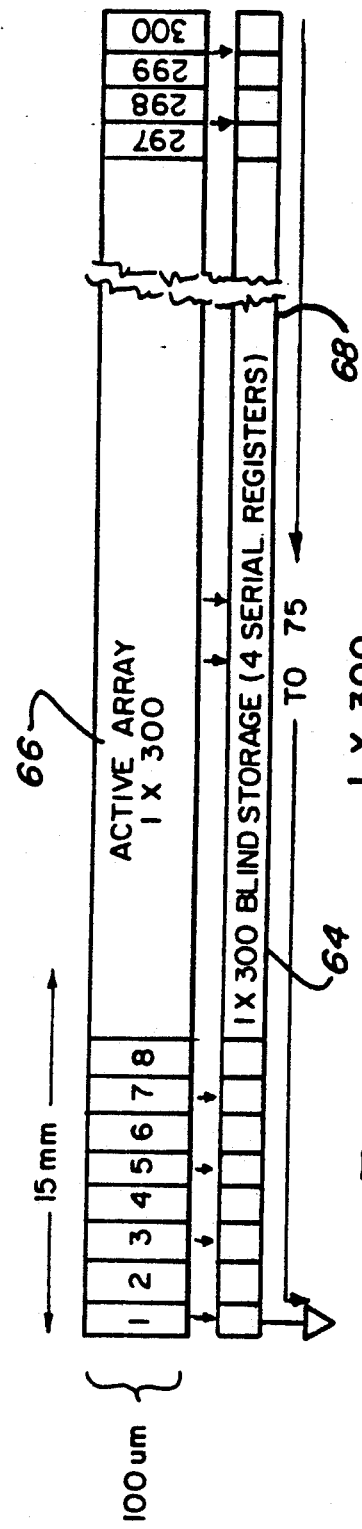
Fig_12

SUBMICRON DIAMETER PARTICLE DETECTION UTILIZING HIGH DENSITY ARRAY

FIELD OF THE INVENTION

This invention relates to submicron particle detection, and, more particularly, relates to a device and method for submicron particle size detection utilizing a high density array.

BACKGROUND OF THE INVENTION

The lower limit of particle sizing in a gas (including air) by scattering due to illumination (such as provided by a laser source) is limited by noise generated by the background light produced by scattering from gaseous molecules. In particular, when the volume illuminated is large, as is required, for example, for high sample volume flow, when pressures are high raising molecular density, or when the intensity of illumination is itself sufficiently high, the scattering by molecules within the "viewing volume" can exceed that of the smallest particle attempting to be sized by manyfold.

In a similar manner, the intrinsic scattering by liquids limits the ability to measure extremely small particles therein. In addition, with respect to surfaces, the scattering from surface roughness, texture, or morphological material state similarly limits how small contaminants, or contaminating particles, can be sized or point defects measured.

To develop practical aerosol instruments capable of detecting submicron particles with high sensitivity in the presence of a high molecular scattering environment, it has been found necessary to employ multi-element detectors in combination with imaging systems of high light gathering power to divide the illuminated volume a sufficient number of times so that the molecular scattering background and its noise do not mask the scattering by the particles of interest (see my U.S. Pat. Nos. 4,798,465 and 4,893,928 wherein the use of gas as the fluid, multi-element linear arrays having typically ten to twenty elements covering a 1×10 μm field, as the detector, and electronics for processing enable the device described to have a particle sizing sensitivity at least as low as 0.1 μm diameter at a flow rate of 1 cfm using a 1 watt laser cavity, and also see my pending U.S. patent Application Ser. No. 07/919,983, and application is a continuation of U.S. patent application Ser. No. 07/505,831 now abandoned, and describes a device wherein liquid is utilized as the fluid).

In general, the higher the pixel density (i.e., number of elements utilized), the greater the noise reduction.

SUMMARY OF THE INVENTION

This invention extends the capabilities of prior devices and methods to enable more efficient and/or still smaller particle sizes to be detected by effectively reducing molecular scattering associated with such devices to such low levels that it becomes substantially a non-limiting factor. This is accomplished through the use of a high density array and/or associated specialized illumination and/or processing.

In one embodiment of this invention, a high pixel density two dimensional (2D) array is utilized in combination with detector storage and intermediate parallel-to-serial conversion to greatly limit the number of final parallel processing channels needed, with illumination of the scattering particles detected by the array being modified as to direction of impingement and/or shape.

With respect to beam shaping, the beam may be shaped either to an elliptical or to a circular cross-section typically focussed so that the beam converges to a focal point, preferably centered within the sensing region to achieve maximum energy density (sensitivity), and then diverges from the focal point.

It is therefore an object of this invention to provide an improved submicron particle detection device and method.

It is another object of this invention to provide an improved submicron particle detection device and method that utilizes a high density array to detect scattered light.

It is still another object of this invention to provide an improved submicron particle detection device and method that utilizes a beam of illumination that is particularly shaped and/or directed.

It is yet another object of this invention to provide an improved submicron particle size detection device and method that utilizes a high density array and a beam of illumination that is at least one of elliptical and circular cross-section.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiments of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIGS. 1A and 1B are diagrams illustrating air flows intersecting with a laser beam (as described in U.S. Pat. No. 4,798,465);

FIG. 2 is a diagram illustrating the use of a linear detector array and an associated imaging system to localize small volumes within a laser beam (as also described in U.S. Pat. No. 4,798,465);

FIG. 3 is a diagram similar to that of FIG. 2 but illustrating the use of a high density detector array in conjunction with an associated imaging system according to this invention to localize still smaller volumes within a laser beam;

FIG. 4A is a block diagram illustrating focussing of a laser beam directed through the sensing region;

FIG. 4B is an illustration of a focussed beam utilized at the sensing region with the beam being shown to converge to a substantially centrally positioned focal point within the sensing region and then diverging therefrom;

FIG. 5 is a diagram illustrating the use of a high density detector array and an associated refracting imaging system together with beam shaping optics for causing the beam to be astigmatic (elliptical) when passing through the sensing region;

FIG. 6 is a diagram illustrating the system as shown in FIG. 5 with the system rotated 90° relative to that shown in FIG. 5;

FIG. 7 is a diagram similar to that of FIG. 6 but showing the imaging system in a reflecting configuration;

FIG. 8 illustrates relative image sizes at various positions of particles in passing through the astigmatic beam as shown in FIGS. 5, 6 and 7;

FIG. 9 is an illustrative presentation of a two dimensional high density detector array utilizing blind storage;

FIG. 10 is a block and schematic diagram of the invention illustrating micro-computer controlled parallel processing in conjunction with a high density array and digital storage;

FIG. 11 graph of total scattering crosssection versus particle diameter utilizing the device of FIGURE 10; and FIG. 12 illustrates a high density detector array having a single-sided charge storage (a double-sided charge storage, while not shown, could also be utilized) with the device being designed for particular use in conjunction with the focussed beam as shown in FIG. 4.

DESCRIPTION OF THE INVENTION

To achieve detection of particles having a diameter of 0.1 $\mu$m and larger at 1 cfm flow rate, a low density linear array was effectively utilized as described in my U.S. Pat. No. 4,798,465 (which patent is hereby included by reference).

In this invention, a high density (linear or 2D) array is utilized to achieve detection of submicron particles, and a high density detector array, utilized in conjunction with a focused or non-focussed beam having either an elliptical or circular cross-section, can achieve detection of particles much smaller than 0.1 $\mu$m at high flow rates.

For use with an elliptical beam (as is now preferred when utilizing a 2D detector array), fundamental changes are utilized for the flow and optics system. To illustrate, consider a flow system and collecting optics as shown in FIGURES 1a, 1b and 2 (which FIGURES are taken from U.S. Pat. No. 4,798,465). In such a system, laser beam 15 is directed through sensing region 16 which also receives a fluid having particles therein through conduit 17. Particle images at sensing region 16 are localized to individual elements 18 of array 19 by imaging system 21 and a particle's image scans completely across a particular element during transit of the particles through the laser beam.

If particle images sensed at sensing region 16 are coupled through imaging system 21 to a high density array 23 (as indicated in FIG. 3), the energy of the scattered light is shared by all elements 24 of the array in a vertical column. While this would negate the full noise reduction advantage offered by a 2-D array with its higher pixel density, it nevertheless allows efficient submicron particle detection similar to that afforded by the device shown in U.S. Pat. No. 4,798,465.

To achieve greater advantage, the energy must be localized as much as possible to a single pixel. Such improvement can be achieved utilizing the flow and optics system described in U.S. Pat. No. 4,798,465 by focussing the beam from laser 26, as indicated in FIG. 4A, using beam shaping optics 27 to focus the beam directed to sensing region 28 (it is also to be realized that the laser cavity itself could have a focus positionable within the sample region thus eliminating the need for separate beam shaping optics). Focussing of the beam can cause the beam to converge or diverge in passing through the sensing region, and may be caused to both converge and diverge by causing the beam to have a focus 29 within the sensing region (and preferably centrally located within the sensing region as illustrated in FIG. 4B utilizing a circular beam).

In order to provide optimum localization of particle scattering energy, however, an arrangement as shown in FIGS. 5 and 6 (or alternately in FIG. 7) is employed.

As indicated in FIG. 5, the beam is optically shaped by beam shaping optics 30 so that the laser beam 31 is ideally made highly astigmatic (elliptical). This reduces the volume of molecular gas that must be viewed, and the required depth-of-focus is also reduced by limiting the depth-of-field permitting larger collecting solid angles.

The particle-containing fluid (gas (normally air) is utilized as particularly discussed herein, but it is to be realized that a liquid could also be utilized as the particle-containing fluid) is directed towards the collecting optics orthogonal to the object plane instead of paralleling the object plane as has been previously and more conventionally used. In addition, the fluid is directed parallel to the optical axis of the collecting optics. To effect this arrangement, fluid inlet 33 directs the fluid through laser beam 31 (at sensing region 28) and channel 34 (at, or adjacent to, imaging system 35) to outlet 36 adjacent to first element 37 of optics system 35 (while not specifically shown, the first element 37 could be cored to allow channel 34 to pass through the first element, with outlet 36 being then positioned at the side of the first element opposite to that shown in FIGS. 5 and 6).

Imaging system 35 is shown as a refracting configuration in FIGS. 5 and 6 with the optical images being directed by the imaging system to high density detector array 23. As indicated in FIG. 7, a reflecting configuration 38 may also be utilized, and, as shown, may be embodied by providing a central hole, or aperture, 39 in first element 40 through which fluid from inlet 33, after passing through laser beam 31, passes to outlet 42.

Regardless of optical system choice, an essential feature of such a system is that all particles pass through the object plane whereat they are in exact focus, and their scattered energies are localized to the theoretical extent offered by the resolving power of the collecting optics employed. An important attribute of the optical system is that it be designed as a flat-field system (to minimize field curvature). For diffraction limited objectives, the dimensions of such an image from a submicron particle are on the order of the wavelength of illumination used and independent of particle size.

The minor axis of laser beam 31 is made as narrow as practical to keep the depth-of-field as short as possible. This is necessary, since the image formed as the particle enters and exits on opposite sides of the object plane is much larger than at the object plane where the particle is in best focus (this can be noticed, for example, when focussing a microscope on a small defect or particle). FIG. 8 diagrams the circle-of-least confusion (effective image size) of a small (e.g., submicron) particle during laser beam transit. The maximum image diameter is solely a function of the depth-of-field ($D_f \approx$ laser beam width) and numerical aperture (N.A.) of the collecting optics according to: maximum image diameter $\approx 2 D_f \times$ N.A.. Thus, if N.A. is 0.5 and the $D_f$ is $\pm 50$ $\mu$m, the image is also 50 $\mu$m Dia. when entering and exiting the laser beam.

When optimizing pixel size in a 2-D array with illumination as just described, the array pixel size is matched to the maximum image size to achieve the maximum signal-to-noise advantage. It should be obvious that if a 1×10 mm field were to be covered using 50 μm elements, the pixel density would be enormous having increased by a factor of 400× over that of a 10-element array having 1×1 mm elements. While parallel processing 4,000 elements is straightforward, it is both costly and impractical.

A solution is offered by high density detection devices that integrate and store light signals which allow for parallel-to-serial data transfer. Such high density detection devices can be utilized with one or more charge storage units (blind or otherwise). The most common devices in this category are charge coupled devices (CCD's). CCD's are known devices that store charges in potential wells and transfers this charge almost completely as a packet by translating the position of the potential wells. CCD's are currently manufactured with over 1,000,000 pixels. Typical pixels of high resolution CCD cameras are 25 μm in size and can be manufactured as small as 5 μm and as large as 200 μm without large sacrifices in performance.

For the application set forth herein, a customized configuration of high density array 23 is optimal. Such an array is shown in FIG. 9. This CCD array has a 20×200 pixel (1×10 mm) light sensitive region 44 with dual 10×200 charge storage regions 46 and 47.

In operation, the light sensitive region is aligned to view the 1×10 mm field of interaction between the sample inlet flow and the laser beam. The light scattered by possible particles and ever present molecules of air is integrated for a period of time which is designated as an image frame time. The image is transferred to the top and bottom storage arrays by shifting each half image in opposite directions. This transfer process is a "frame dump" requiring only a few microseconds. The frame dump also clears the active array of all charge.

After a frame dump, the active light sensitive region starts a new integrating light collection period. The collecting period is generally long compared to the average transit time of a given particle or the frame dumping time. This allows time for the storage buffers to be read out, analysis for possible particle scattering events, and the affected pixel data digitized for particle size determination.

A typical data collection and readout cycle can be described in conjunction with the block diagram of the device as set forth in FIG. 10. The 20×200 pixel active array collects one frame of charge data over 100μ seconds. This data is transferred to alternate 10×200 pixel storage arrays (such as blind storage arrays) in a few microseconds, clearing all charge from the active array and restarting a new collection cycle. The data now stored in the charge storage array is parallel transferred to one of eight serial registers 48 (four in each charge storage unit) and then serially transferred to one of eight output ports (four in each charge storage unit) wherein it is amplified to high level. Of course, a single serial output could also be used with a longer integration period minimizing data processing electronics needed.

The eight outputs (four from each storage unit) are parallel processed by parallel processor units 49 and 50. Each parallel processor includes a threshold detector for each output (threshold detectors 52 and 53 are indicated in FIG. 10) and each threshold detector is a voltage comparator set to a signal level equivalent to the smallest particle size of interest or just above background noise peaks if maximum sensitivity is sought. The outputs from each of the threshold detectors are coupled to free running analog-to-digital (A/D) converters 55 and 56 (A/D converters are indicated in FIG. 10 to be connected with threshold detectors 52 and 53, respectively), and the A/D converters consistently convert the analog data stream to digital data. When a pixel has received charge values greater than threshold, the comparator signals the A/D to transfer to a digital storage address determined by an address counter in microprocessor controller (MPC) 58 having digital storage units 60 and 62 connected therewith. The MPC then adds all charge values stored for a data frame to determine particle size.

For most particle events, only a few pixels accumulate any charge above threshold. The normal capacity of a single pixel is between 100,000 and 1,000,000 $e^-$ (where $e^- =$ electrons). When a pixel fills up, excess charge accumulates in adjacent pixels. There is also a significant probability of a particle image overlapping 2–4 elements due to chance positioning.

In addition to the greatly increased sensitivity afforded by the noise reduction, data processing for such a system offers several opportunities not possible from any other known technologies: 1) Non-uniformities in the light field can be compensated for by using the D.C. molecular scattering as a measure of illumination intensity (an addressed calibration map can then be referred to to normalize all data); 2) Potential optical coincidence errors can be largely removed by requiring adjacency in affected pixels; 3) Sensitivity can be made a function of flow rate since transit time is proportional to signal accumulated; and 4) Beam divergence resulting in intensity reduction is automatically compensated for in one direction (the flow direction) because the energy is integrated for the entire transit independent of the beam width in the flow direction.

Storage buffers 60 and 62 may be read out through individual or multiple ports or taps. The greater the number of output ports, the shorter the analysis time or, alternatively, the greater the possible pixel number (eight such ports are indicated in FIGS. 9 and 10). These ports involve on-chip, low-noise monolithic amplifiers and can provide high level outputs. State-of-the-art slow-scan CCD's today are capable of generating rms noise levels of a few electrons/pixel at 100 kilohertz transfer rates. In general, the noise level increases with operating speed similar to most electronic devices but it is still only tens of electrons per pixel at 10 megahertz rates.

In the application illustrated herein, the electronic noise level is somewhat higher than in known slow-scan CCD low-light level imagers due to the finite contribution from molecular scattering and a desired increased operating speed. Molecular scattering can only be reduced by reducing the time period for data collection or reduction in pixel size. Since this requires increased operating speed with coincident increased electronic noise, proper system optimization for lowest noise requires consideration of both electronic and molecular scattering noise sources in combination. The molecular scattering is effectively a D.C. background light level which is integrated over the integration cycle. The noise associated with this D.C. light level, as with all light signals that are shot noise limited, is proportional to the square root of the D.C. light level.

For performance evaluation purposes, it is simpler to convert all signals to integrated numbers of converted electrons and perform statistical noise estimates from them. An rms value of $10e^-$ can be assumed for electronic noise. The quantum efficiency of CCD's is ordinarily at least 50% and can approach 100% with optimized diffusions. Therefore, if the total number of photoelectrons generated during an integration cycle by molecular scattering is 100, this rms noise level is $\approx \sqrt{100} \approx \pm 10e^-$. A system design would be optimal when the noise from molecular scattering is reduced to a value comparable to that of the intrinsic array electronics or when the quadratic sum of all noise sources is minimum. If the electronics and molecular scattering each generated an rms value of $\pm 10e^-$, for example, the quadratic sum of these two equal sources would be $\sqrt{(10)^2+(10)^2} \approx \pm 14e^-$.

The light signals generated by molecular scattering can be simply calculated using Rayleigh theory or measured photometrically. A major simplification in computations exists for the particles when they are very small compared to the wavelength. In such cases, the particle's scattering pattern is identical to that of the molecules and the same theoretical simplifications apply (see Knollenberg, "The Measurement of Particle Sizes Below 0.1 Micrometers", Journal of Environmental Sciences, Jan./Feb. 1985, pages 32-51). For larger particles, Mie theory must be used.

FIG. 11 is a computed theoretical curve showing the total scattering cross sections ($C_{SCA}$) of submicron particles extending into the molecular range. The scattering cross-section of a molecule of air with a diameter of $\approx 4 \text{Å}$ is seen to be $\approx 10^{-27} \text{cm}^2$. Multiplying the scattering cross section by the illumination power density (P/A, in Watts/unit area) results in the scattered power per particle, or molecule. The collected light signal will be only that fraction afforded by the collecting solid angle. Assuming the collected fraction to be 10% and restricting consideration to Rayleigh particles that scatter similarly to molecules, the collected power generated by a particle ($P_p$) or molecule is found by: $P_p = 0.1 \times C_{CSA} \times P/A$ when $C_{CSA}$ and A are in the same units (e.g., $\text{cm}^2$). If a laser or laser cavity is used generating 0.5 Watts and having a $0.1 \times 0.01$ cm cross-section as illustrated in FIG. 8, the power density is $0.5 \text{ W}/10^{-3} \text{ cm}^2 = 500 \text{ W cm}^{-2}$.

For the molecular scattering case, the contributions from an ensemble of scatterers must also be added since no volume can be made sufficiently small to isolate individual molecules by an optical system at ambient pressures. For a sample beam, as illustrated in FIG. 8, there is a volume of $2.5 \times 10^{-7} \text{ cm}^3$ associated with an individual pixel which is $50 \times 50 \times 100$ $\mu$m. The molecular density of air at standard temperature and pressure is $\approx 2.8 \times 10^{19}$ molecules/$\text{cm}^3$. Each pixel thus continuously sees $7 \times 10^{12}$ molecules. The total molecular scattered power generated by a laser beam having 500 W $\text{cm}^{-2}$ power density is thus 500 W $\text{cm}^{-2} \times 10^{-27}$ $\text{cm}^2$/molecule $\times 7 \times 10^{12}$ molecules/pixel volume $= 3.5$ $10^{-12}$ Watts/pixel volume. With 10% collection efficiency, this becomes $3.5 \times 10^{-13}$ Watts/pixel.

To convert to charge, it is necessary to form the product of Responsivity (amps/watt), the collected power and integration time which is assumed to be $10^{-4}$ seconds Assuming 0.5 A/W Responsivity, this generates $17.5 \times 10^{-18}$ Amp-Sec or coulombs. Dividing the collected charge in coulombs by the charge on an electron ($1.6 \times 10^{-19}$ coulombs) gives the number of photoelectrons generated. Thus, $$\frac{17.5 \times 10^{-18} c}{1.6 \times 10^{-19} c/e^-} = 110 e^-$$

and the rms noise is $\approx \sqrt{110}$ or $\approx 10 e^-$.

For this same illumination circumstance, the photocurrent generated by a single 0.1 $\mu$m polystyrene latex (PSL) calibration particle with a scattering crosssection of $2 \times 10^{-12} \text{cm}^2$ is $2 \times 10^{-12} \text{cm}^2 \times 10\% \times 500$ W $\text{cm}^{-2} \times 0.5$ A/W $= 5 \times 10^{-11}$ A. However, in this case the integration time is the particle transit time.

For a 1 cfm flow through a $1 \times 10$ mm cross section of the laser beam in FIG. 8, this is $\approx 2$ microseconds. Thus, the signal is:

$$2 \times 10^{-6} \sec \times 5 \times 10^{-11} A = 10^{-16} c \text{ or } 680 e^{-1}$$

providing a signal to rms noise ratio of 68:1 neglecting electronic noise. Such a system can reach 0.05 $\mu$m at 1 cfm with less laser power than required by the linear array previously used to reach 0.1 $\mu$m. Only about 10 mw are actually required for 0.1 $\mu$m sensitivity at 1 cfm. This is 100 times less illuminating power than required by the device shown in U.S. Pat. No. 4,798,465 with a 10 element linear array.

If the flow rate is reduced to 1/50 cfm, the particle signal integration time would equal the molecular scattering integration time providing maximum signal-to-noise advantage. A signal-to-rms noise ratio of $50 \times 68 = 3400:1$ would exist for a 0.1 $\mu$m particle enabling particle detection in the 0.02 to 0.03 $\mu$m range.

The sensitivity-flow rate product can be seen to be a figure-of-merit for any detection scenario, that is, flow rate can obviously be traded off for increased sensitivity, and vice versa. The ability to achieve a given sensitivity-flow rate product at a lower level of illumination is of additional advantage.

If a 10 W cavity is chosen, sensitivity below 0.05 $\mu$m at 1 cfm is comfortably achieved. In this case (and maintaining the same integration time), the molecular scattering dominates the noise because the laser power has been increased $20 \times$. The S/N would increase by the square root of the power ratio or $\approx \sqrt{20} = 4.6 \times$. Again, to reduce noise dominated by molecular scattering, the readout time should be reduced until the electronic noise and molecular scattering noise again balance. The optimum integration time would depend upon exact array device noise characteristics and how they vary with operating speed. By slowing the flow rate, still smaller sizes are again detectable.

Another use of on-board pixel storage is an application to linear arrays in conjunction with circular beams. Consider the situation when still higher sensitivity is sought at the maximum possible flow rate. In this situation, the laser beam is focused to about 100 $\mu$m as a circular beam (as shown in FIG. 4B). The laser beam converges and diverges in both dimensions passing through focus 29. The path length over which the laser intensity can be considered constant is somewhat a discretionary matter but, if limited to regions where the intensity is at least 50% of the maximum at focus, a working region 15mm long is possible with a $0.1 \times 15$ mm field (as shown in FIG. 4B). At sonic flow (340 m/sec), a flow rate of 1 cfm is possible. The transit time for a particle is $\approx 0.2 \mu$ Sec.

FIG. 12 shows a linear detector arrangement 64 matched to such an illuminated volume. In this case, there is no advantage in orienting the flow towards the lens since each detector pixel (element) views across the full beam width. However, a high density array still offers advantages in noise reduction, and the ability to transfer and store provides a parallel to serial transfer process that minimizes the number of parallel processing channels required.

In the array shown in FIG. 12, an active region 66 consisting of 300 50 $\mu m \times 150$ $\mu m$ elements are used which frame dump into a 300 pixel storage buffer. Four taps, or output ports, transfer 75 pixels each from storage buffer 68. Running at 7.5 mHz, the serial data streams are transferred out every 10$\mu$seconds. Here the molecular scattering per pixel is 20$\times$greater than with respect to the arrangements shown in FIG. 9, since each column is single, rather than 20 pixels high. However, the time between frames is only 1/10 as long resulting in a net increase in the integrated molecular scatter of only a factor of 2. The signal has increased by a factor of 10$\times$because the beam cross-sectional area is reduced by 10$\times$resulting in an overall S/N improvement of $10/\sqrt{2}$ or $\approx 7x$.

Because of flow divergence at sonic speeds, the primary advantage of such a linear system is at slow flow rates slowing the particle transit time to integrate a larger sum of photons. At 0.1 cfm, a 2$\mu$ Sec transit time results in a 70$\times$ sensitivity increase over that of the arrangement shown in FIG. 9 at 1 cfm. At 0.02 cfm, the S/N is maximum and sensitivities of 0.02 $\mu m$ can be readily achieved.

Finally, a focussed circular beam 10 $\mu m$ in diameter could also be used (instead of 100 $\mu m$ as illustrated in FIG. 4B) along with an imaging system with 10$\times$magnification to divide the beam into three hundred 5 $\mu m$ $\times 10$ $\mu m$ pixel viewing segments covering a 1.5 mm beam length. A 10 Watt laser cavity generated beam waist would achieve $\approx 10MW/cm^2$ power density. A 0.01 $\mu m$ particle having a scattering cross-section of $10^{-18} cm^2$ would scatter $10^{-11}$ Watts which an optical system would collect 10% of, thus generating $10^{-12}$ Watts of signal power. The molecular scattering signal power for a $5 \times 10 \times 10$ $\mu m$ volume is approximately $10^{-11}$ Watts. Integration times $>10\mu sec$ provide readily detectable 0.01 $\mu m$ particles at 0.0001 cfm.

As can be appreciated from the foregoing, this invention thus offers an improved device and method for effecting enhanced submicron diameter particle detection utilizing a high density array.

What is claimed is:

1. A submicron particle detection device, comprising:
a sensing region capable of having submicron particles thereat;
illuminating means providing a beam directed toward said sensing region wherein said submicron particles at said sensing region cause light scattering;
detecting means including a charge coupled device high density array means having a plurality of image pixels for receiving light scattered by said submicron particles at said sensing region whereby a charge is created on each of said pixels receiving said light, the charge on each said pixel being transferred therefrom by sequential transfer of charge from each individual pixel to the next adjacent pixel until complete transfer of the entire image of the array has occurred; and
processing means for receiving said charge outputs from said detecting means and, responsive thereto, processing the same to provide an output indicative of said submicron particles.

2. The device of claim 1 wherein said sensing region is capable of receiving a fluid that is one of a gas, including air, and a liquid, with said fluid having said submicron particles therein.

3. The device of claim 1 wherein said sensing region includes a surface having contaminating submicron particles thereon causing light scattering.

4. The device of claim 1 wherein said sensing region is bounded in part by conduit means for passing said fluid through said sensing region, wherein said conduit means is configured to cause said fluid to flow through said sensing region at a volumetric rate sufficiently high to cause a high molecular scattering background to be present at said sensing region, and wherein said high density array means, in conjunction with said illuminating means and processing means, enables said output to be highly sensitive of the size of said submicron particles despite the presence of said high molecular scattering background.

5. The device of claim 1 wherein said beam has a cross-section within said sensing region that is least one of elliptical and varying diameter.

6. The device of claim 1 wherein said beam has a circular cross-section.

7. The device of claim 1 wherein said beam has a focus with said beam converging toward said focus and then diverging from said focus.

8. The device of claim 7 wherein the focus of said beam is substantially centrally positioned within said sensing region.

9. A submicron particle detection device, comprising:
a sensing region capable of having submicron particles thereat;
illuminating means providing a beam directed toward said sensing region wherein said submicron particles at said sensing region cause light scattering;
detecting means including high density array means for receiving light scattered by said submicron particles at said sensing region and providing charge output signals indicative thereof;
potential well charge storage means for receiving said charge outputs transferred from said high density array means and providing stored charge outputs; and
processing means connected with said charge storage means for receiving said stored charge outputs therefrom and, responsive thereto, processing the same to provide an output indicative of said submicron particles.

10. The device of claim 9 wherein said charge storage means includes first and second blind storage units for receiving different portions of each data frame transferred from said high density array means.

11. The device of claim 9 wherein said processing means includes parallel processing means having serializing means whereby the output from said charge storage means is serialized into one or more serial streams.

12. The device of claim 11 wherein said parallel processing means includes threshold detector means for establishing the minimum size of said submicron particles to be sized, and analog-to-digital detector means to provide a digital output.

13. The detector of claim 12 wherein said processing means includes digital storage means for receiving the digital output from said analog-to-digital detector and a micro-computer for controlling operation of said device and providing said output indicative of the size of said submicron particles.

14. A submicron diameter particle size detection device, comprising:
   conduit means for receiving a fluid having particles of submicron diameter therein with said fluid being capable of flowing through a predetermined sensing region of said conduit means;
   a laser providing an elliptical beam directed through said sensing region such that said fluid is caused to pass orthogonal the narrowest portion of said beam to cause light scattering by particles present in said sensing region;
   high density array means for receiving and detecting light scattered by particles present in said fluid at said sensing region;
   first and second charge storage means for receiving a different portion of each data frame transferred from said high density array means;
   first and second parallel processing means connected with different ones of said first and second charge storage means to receive and process the outputs from said charge storage means and provide an output indicative thereof; and
   computer means for controlling operation of said device and providing an output indicative of the size of said submicron particles in said fluid.

15. The device of claim 14 wherein each of said parallel processing means includes a threshold detector for determining the minimum size of said submicron particles to be sized.

16. The device of claim 14 wherein each of said parallel processing means includes analog-to-digital means for providing a digital output, and wherein said device includes digital storage means to receive said digital output from said analog-to-digital means.

17. The device of claim 14 wherein said output is provided by said computer means is indicative of particles at least as small as 0.01 microns.

18. The device of claim 17 wherein said flow of fluid through said sensing region causes a high molecular scattering background to be present, and wherein said particle size at least as small as 0.01 $\mu$m is still detected by said device.

19. The device of claim 14 wherein said device includes imaging means for directing said light scattered at said sensing region to said high density array means.

20. The device of claim 19 wherein said imaging means includes refracting means.

21. The device of claim 19 wherein said imaging means includes reflecting means.

22. The device of claim 19 wherein said imaging means includes at least one imaging element, and wherein said conduit means causes said fluid to be directed toward said imaging means substantially orthogonal to the object plane of said imaging element and substantially parallel to the optical axis of said imaging element.

23. The device of claim 22 wherein said imaging element has a central aperture, wherein said fluid is directed into said aperture, and wherein said conduit means includes outlet means for receiving fluid passing through said aperture.

24. A submicron diameter particle sized detection device, comprising:
   conduit means capable of receiving a fluid having submicron diameter particles therein and passing said fluid through a predetermined sensing region of said conduit means;
   laser means providing a focussed beam that converges to a focus and then diverges from said focus, with said beam being directed through said sensing region such that the focus of said beam is substantially centrally located in said sensing region;
   a charge coupled device high density array means having a plurality of image pixels for receiving and detecting light scattered by particles present in said fluid at said sensing region whereby a charge is created on each of said pixels receiving said light, the charge on each said pixel being transferred therefrom by sequential transfer of charge from each individual pixel to the next adjacent pixel until complete transfer of the entire image of the array has occurred;
   charge storage means for receiving said charge outputs from said charge coupled device high density array means;
   parallel processing means connected with said charge storage means to receive and process the serialized charge outputs from said charge storage means and provide an output indicative thereof; and
   computer means for controlling operation of said device and providing an output indicative of the size of said submicron particles in said fluid.

25. The device of claim 14 wherein said beam within said sensing region is about 15 mm in length and wherein said high sensitivity array includes about 300 elements.

26. The device of claim 25 wherein said device has a sensitivity such that said device can detect particles smaller than 0.01 microns.

27. A process for detecting submicron particles utilizing light scattering, said process comprising:
   providing a sensing region;
   introducing fluid having submicron particles therein into said sensing region;
   illuminating said sensing region to cause scattering of light by submicron particles;
   providing a charge coupled device high density array having a plurality of image pixels;
   utilizing said charge coupled device high density array to detect light scattered by particles at said sensing region whereby a charge is created on each of said pixels receiving said light, the charge on each said pixel being transferred therefrom by sequential transfer of charge from each individual pixel to the next adjacent pixel until complete transfer of the entire image of the array has occurred; and
   processing said transferred charge outputs from said pixels to provide an output indicative of said submicron particles.

28. The process of claim 27 wherein said process includes forming a beam having a cross-section that is at least one of elliptical and focussed so that the beam converges toward said focus and diverges from said focus, and utilizing said beam to illuminate said sensing region.

29. The process of claim 28 wherein said method includes focussing said beam so that the focus of the beam is substantially centrally positioned within said sensing region.

30. The process of claim 27 wherein said process includes providing imaging means for transferring said light scattered by submicron particles at said sensing region to said high density array, and wherein said process includes directing fluid into said sensing region in a direction substantially orthogonal to the object plane of said imaging means and substantially parallel to the optical axis of said imaging means.

31. A process for detecting submicron particles utilizing light scattering, said process comprising:
providing a sensing region;
introducing fluid having submicron particles therein into said sensing region;
illuminating said sensing region to cause scattering of light by submicron particles;
providing a high density array;
utilizing said high density array to detect light scattered by particles at said sensing region and providing charge outputs;
providing potential well charge storage means for receiving said charge outputs from said high density arrange means and providing stored charge outputs; and
utilizing the stored charge outputs from said charge storage means for processing via serializing data into at least one output.

32. The process of claim 31 wherein said serialized data is parallel processed with said parallel processing including utilization of a threshold detector for establishing the minimum size of said submicron particles to be sized, and an analog-to-digital detector to provide a digital output.

33. The process of claim 31 wherein said processed output is indicative of submicron particles having a diameter at least as small as 0.01 microns in the presence of a high molecular scattering background at the sensing region.

34. The process of claim 31 wherein said process includes providing a pair of blind storage means each of which receives one-half of each data frame transferred from the high density array means.

35. The process of claim 34 wherein said process also includes utilizing a pair of parallel processing means each of which receives the output of a different one of the pair of blind storage means.

* * * * *